United States Patent
Makuuchi et al.

(10) Patent No.: US 9,779,912 B2
(45) Date of Patent: Oct. 3, 2017

(54) INSPECTION DEVICE AND MEASUREMENT DEVICE

(71) Applicant: Hitachi High-Technologies Corporation, Minato-ku, Tokyo (JP)

(72) Inventors: Masami Makuuchi, Tokyo (JP); Takahiro Jingu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/109,726

(22) PCT Filed: Dec. 8, 2014

(86) PCT No.: PCT/JP2014/082359
§ 371 (c)(1),
(2) Date: Jul. 5, 2016

(87) PCT Pub. No.: WO2015/107795
PCT Pub. Date: Jul. 23, 2015

(65) Prior Publication Data
US 2016/0322193 A1 Nov. 3, 2016

(30) Foreign Application Priority Data
Jan. 20, 2014 (JP) ................................. 2014-007429

(51) Int. Cl.
*H01J 37/00* (2006.01)
*H01J 37/244* (2006.01)
(Continued)

(52) U.S. Cl.
CPC .......... *H01J 37/244* (2013.01); *A61B 5/0059* (2013.01); *G01N 21/94* (2013.01);
(Continued)

(58) Field of Classification Search
CPC .......... H01J 37/244; H01J 49/00; H01J 37/28; H01J 2237/2444; H01J 2237/24495;
(Continued)

(56) References Cited

U.S. PATENT DOCUMENTS

| 8,831,899 B2 * | 9/2014 | Nemoto | ............. | G01N 21/9501 356/237.5 |
| 2005/0092899 A1 | 5/2005 | Wolf et al. | | |

(Continued)

FOREIGN PATENT DOCUMENTS

| JP | 58-143251 A | 8/1983 |
| JP | 2002-184470 A | 6/2002 |

(Continued)

OTHER PUBLICATIONS

International Search Report (PCT/ISA/210) issued in PCT Application No. PCT/JP2014/082359 dated Mar. 17, 2015 with English translation (Four (4) pages).

(Continued)

*Primary Examiner* — Michael Maskell
(74) *Attorney, Agent, or Firm* — Crowell & Moring LLP (57) ABSTRACT

A detection circuit for accurately detecting a very small foreign material and an inspection/measurement device using the same are provided. The inspection/measurement device includes: an irradiation section that irradiates a laser beam to a surface of a specimen; and a detection section that detects scattered light from the surface of the specimen and generates a detection signal. The detection section includes: a photon counting sensor that outputs M output signals from photo-detecting elements of N pixels (M and N are natural numbers, and M<N); M current-voltage conversion sections that execute current-voltage conversion on the output signals of the photon counting sensor respectively; a voltage application section that applies reference voltages to the current- (Continued)

voltage conversion sections; and a detection signal generation section that generates a detection signal on the basis of the outputs of the current-voltage conversion sections.

6 Claims, 7 Drawing Sheets

(51) Int. Cl.

| | | |
|---|---|---|
| G01N 21/956 | (2006.01) | |
| G01N 21/94 | (2006.01) | |
| G01N 21/95 | (2006.01) | |
| H01J 37/28 | (2006.01) | |
| A61B 5/00 | (2006.01) | |
| H01J 49/00 | (2006.01) | |

(52) U.S. Cl.
CPC ....... *G01N 21/9501* (2013.01); *G01N 21/956* (2013.01); *H01J 37/28* (2013.01); *A61B 5/0075* (2013.01); *H01J 49/00* (2013.01); *H01J 2237/2443* (2013.01); *H01J 2237/2444* (2013.01); *H01J 2237/2445* (2013.01); *H01J 2237/24495* (2013.01)

(58) Field of Classification Search
CPC ...... H01J 2237/2443; H01J 2237/2445; G01N 21/9501; G01N 21/94; G01N 21/956; A61B 5/0059; A61B 5/0075
USPC ........ 356/237.1, 237.2–237.5; 250/306, 307, 250/310, 311
See application file for complete search history.

(56) References Cited

U.S. PATENT DOCUMENTS

| | | | | |
|---|---|---|---|---|
| 2006/0092427 A1* | 5/2006 | Nielsen | ............. | G01N 21/9501 356/491 |
| 2008/0304055 A1* | 12/2008 | Oshima | ............. | G01N 21/9501 356/237.5 |
| 2010/0060895 A1* | 3/2010 | Oshima | ................. | G01N 21/47 356/369 |
| 2013/0286386 A1* | 10/2013 | Serikawa | ........... | G01N 21/9501 356/237.5 |
| 2015/0116702 A1* | 4/2015 | Matsumoto | ........ | G01N 21/9501 356/237.5 |
| 2015/0146200 A1* | 5/2015 | Honda | ................ | G01N 21/956 356/237.5 |

FOREIGN PATENT DOCUMENTS

| | | | | |
|---|---|---|---|---|
| JP | 2002-530631 A | 9/2002 | | |
| JP | 2005/526239 A | 9/2005 | | |
| JP | 2007-248255 A | 9/2007 | | |
| JP | 2012-135096 A | 7/2012 | | |
| JP | WO 2013161912 A1 * | 10/2013 | ........... | G01N 21/956 |
| JP | 2013-231631 A | 11/2013 | | |
| JP | 2013-234966 A | 11/2013 | | |
| JP | WO 2013168557 A1 * | 11/2013 | ......... | G01N 21/9501 |

OTHER PUBLICATIONS

Japanese-language Written Opinion (PCT/ISA/237) issued in PCT Application No. PCT/JP2014/082359 dated Mar. 17, 2015 (Five (5) pages).

* cited by examiner

INSPECTION DEVICE AND MEASUREMENT DEVICE

TECHNICAL FIELD

The present invention relates to inspection devices and measurement devices.

BACKGROUND ART

There are some descriptions about the background art of this technical field in Japanese Unexamined Patent Application Publication (Translation of PCT Application) No. 2005-526239 (Patent Literature 1). This publication says, "A mechanism that detects the intensity value of a beam with a comparatively large dynamic range which is emitted from a specimen such as a semiconductor wafer (a beam of scattered light, a beam of reflected light, or a beam of secondary electrons, for example) is provided" (Refer to "Abstract").

In addition, Patent Literature 2 says, "A voltage adjustment device supplying DC voltages to plural elements, comprising: a first supply circuit that supplies a first voltage to the high potential terminals of the elements; and a second supply circuit that supplies plural voltages, which are lower than the first voltage, to the low potential terminals of the elements respectively, in which each of the plural voltages is dependent on the characteristic of the relevant element."

CITATION LIST

Patent Literature

Patent Literature 1: Japanese Unexamined Patent Application. Publication (Translation of PCT Application) No. 2005-526239
Patent Literature 2: Japanese Unexamined Patent Application Publication No. 2012-135096

SUMMARY OF INVENTION

Technical Problem

Patent Literature 1 discloses a mechanism in which, when a beam is irradiated to the surface of a wafer, the intensity of scattered light owing to a foreign material on the surface of a wafer is detected in a comparatively large dynamic range. However, in the case of a device disclosed in Patent Literature 1, if the intensity of scattered light owing to a foreign material becomes very low in accordance with the diameter of the foreign material, dark noises peculiar to a sensor itself make up a large percentage of a detection signal output from the sensor, which makes it difficult to detect a very small foreign material.

In order to solve the above problem, as a photon counting sensor, a semiconductor photo-detecting element such as an MPPC (Multi-Pixel Photon Counter, a registered trademark of Hamamatsu. Photonics K. K.) and a photoelectron multiplier are used as a photodetector.

In a photon counting sensor, as described in Patent Literature 2, in order for a semiconductor photo-detecting element to output a predefined voltage in response to a predefined amount of optical input, means for adjusting an application voltage to the semiconductor photo element has to be installed in a photodetector.

Furthermore, because a laser light source makes pulsed oscillation, if the response speed of the photon counting sensor is not sufficient for the incidence of scattered light, signal components detected by the photon counting sensor decreases, which makes it difficult to detect a very small foreign material.

In addition, in the photon counting sensor, because photo-detecting elements are allocated among several areas, one of which includes several hundreds or more of pixels, there is a possibility that the multiplication factors of the photo-detecting elements are different from each other depending on their locations on the photon counting sensor. In this case, because there are variations between plural output currents flowing out from the photon counting sensor in accordance with the individual light incident parts of the photon counting sensor, the number of photons cannot be identified. Therefore, the photon counting sensor has a problem in that the accurate detection of a very small foreign material becomes difficult because it is necessary to count the number of photons to accuracy of several photons.

In order to solve the above problem, the present invention provides a detection circuit that accurately detects a very small foreign material in a photon counting sensor, an inspection device and a measurement device both of which use the detection circuit.

Solution to Problem

In order to solve the above problem, it is conceivable that the configurations that are described in the appended claims.

This application includes plural means for solving the above problem, and an example of these means is an inspection/measurement device for inspecting or measuring a surface of a specimen. This inspection/measurement device includes: an irradiation section that irradiates a laser beam to the surface of the specimen; and a detection section that detects scattered light from the surface of the specimen and generates a detection signal. The detection section includes: a photon counting sensor that outputs M output signals from photo-detecting elements of N pixels (M and N are natural numbers, and M<N); M current-voltage conversion sections that execute current-voltage conversion on the output signals of the photon counting sensor respectively; a voltage application section that applies reference voltages to the current-voltage conversion sections; and a detection signal generation section that generates a detection signal on the basis of the outputs of the current-voltage conversion sections.

Advantageous Effects of Invention

According to the present invention, a very small foreign material can be accurately detected using a photon counting sensor.

Problems, configurations, and advantageous effects other than those described above will be explicitly shown by explanations about the following embodiments.

DESCRIPTION OF EMBODIMENTS

Hereinafter, the embodiments will be explained with reference to the accompanying drawings.

First Embodiment

A photon counting sensor has been widely used in the fields of semiconductor inspection/measurement devices, medical/healthcare devices, and the like. For example, a semiconductor inspection/measurement device is a device in which electron beams are scanned on a wafer, which is an inspection/measurement target, and irradiated, generated secondary electrons are converted into light using the scintillation phenomenon, a measurement/detection image is generated by detecting this light as a signal, and inspection or measurement is executed on the basis of the measurement/detection image. In the case of inspection/measurement executed on a semiconductor device using this semiconductor inspection/measurement device, because abnormalities or defects in the processes of manufacturing are detected earlier or in advance, the inspection or measurement of patterns on the semiconductor device is executed every time one of the processes of manufacturing is finished.

In this embodiment, in order to accurately detect a very small foreign material, an example of an inspection device, in which the high response of a photon counting sensor to the pulse oscillation of a laser light source is realized, and additionally variations of the light multiplication factors on the device are kept down, will be explained.

Figure 1:
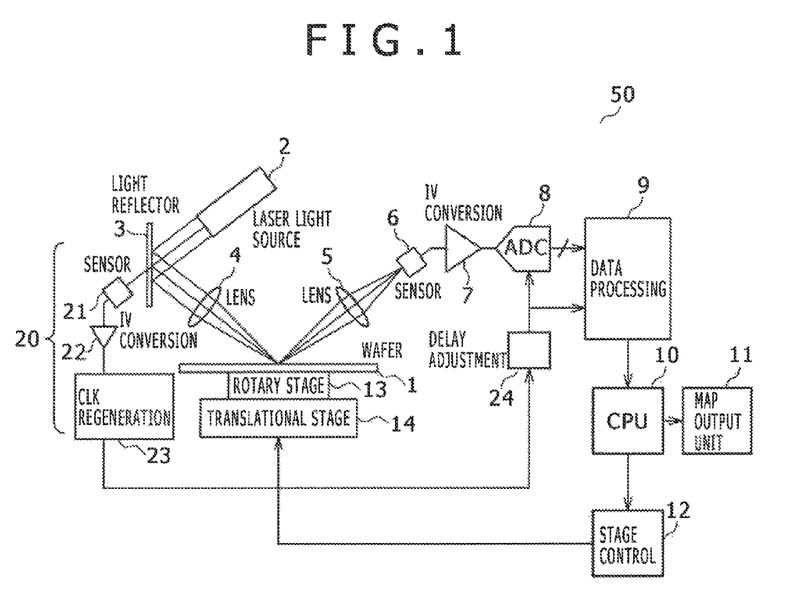
FIG. 1 is an example of a block diagram of an inspection device according to a first embodiment.

FIG. 1 is an example of a block diagram of an inspection device according to this embodiment.

An inspection device 50 includes a laser light 2; a light reflector 3; lenses 4 and 5; a sensor 6; IV conversion 7; an A/D conversion circuit 8; a data processing unit 9; a CPU 10; a map output unit 11; a stage control unit 12; a rotary stage 13; a translational stage 14; a clock detection unit 20; and a delay control unit 24.

In the foreign material inspection device 50, a wafer 1 is fixed on the rotary stage 13, and laser light emitted from the laser light source 2 is irradiated to the wafer 1 via the light reflector 3 and the lens 4. At this time, in the foreign material inspection device 50, the CPU 10 controls the stage control unit 12 in such a way that the wafer 1 is rotated on the rotary stage 13, and then the wafer 1 is moved straight on the translational stage 14. As a result, the laser light irradiated to the wafer 1 has a helical trajectory on the entire surface of the wafer 1, and therefore it is possible to inspect the entire surface of the wafer 1.

The clock detection unit 20 includes a sensor 21; an IV conversion circuit 22; and a clock regeneration circuit 23, and generates a clock signal synchronized with the laser light source 2 using the laser light passing through the light reflector 3.

Figure 2:
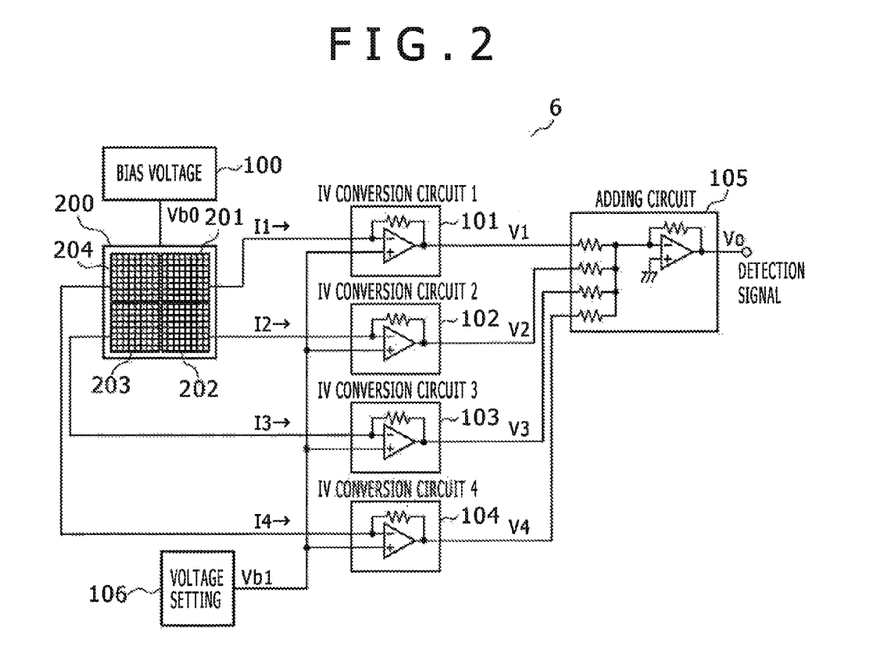
FIG. 2 is an example of a sensor according to the first embodiment.
Figure 3:
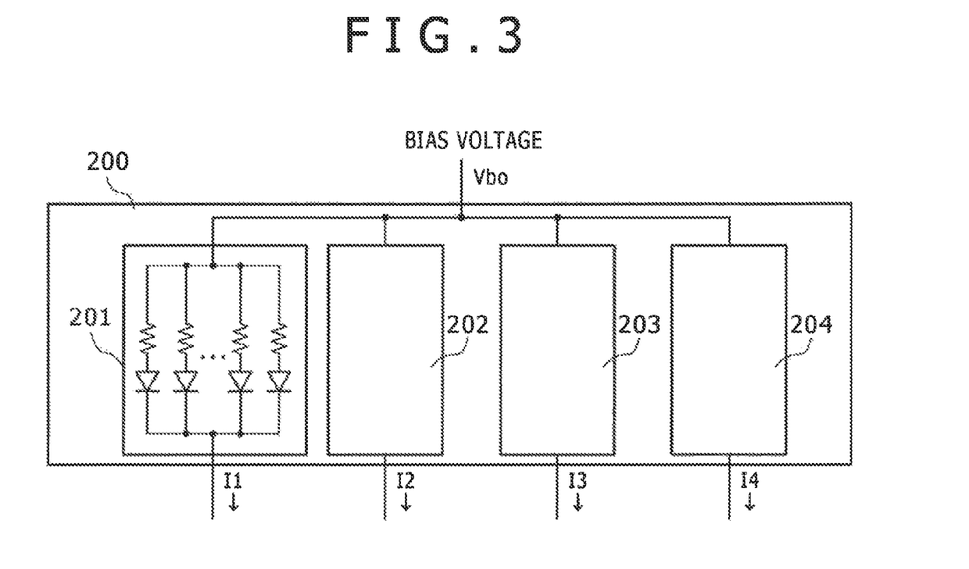
FIG. 3 is an example of a photon counting sensor according to the first embodiment.

In the inspection device 50 according to this embodiment, a delay adjustment is executed on the clock signal generated by the clock detection unit 20 via the delay adjustment unit 24; a detection signal, which is output on the basis of this clock signal by the sensor 6, is amplified by the amplification circuit 7; and the amplified detection signal is sampled by the A/D conversion circuit 8. FIG. 2 is an example of a block diagram of the sensor 6 in the inspection device 50, and FIG. 3 is an example of a block diagram of a molecular grid counting sensor 200 according to this embodiment.

The sensor 6 includes the photon counting sensor 200; a bias voltage setting section 100; IV conversion circuits 101, 102, 103, and 104; an adding circuit 105; and a voltage setting section 106. The photon counting sensor 200 includes photo-detecting elements of N pixels, and as shown in FIG. 3, the outputs are commonized for each of four areas 201, 202, 203, and 204, and output.

The IV conversion circuits 101, 102, 103, and 104 convert the output currents I1, I2, I3, and I4 from the areas 201, 202, 203, and 204 of the photon counting sensor 200 into voltages V1, V2, V3, and V4 respectively, and the adding circuit 105 adds the outputs of the IV conversion circuits 101, 102, 103, and 104, and outputs a detection signal Vo.

The voltage setting section 106 controls a reference voltage to the IV conversion circuits 101, 102, 103, and 104, with the result that the differential voltage between the voltage Vb0 that is output by the bias voltage setting section and the voltage Vb1 that is output by the voltage setting section 106 is applied to the areas 201, 202, 203, and 204 of the photon counting sensor 200.

Assuming that all the values of resistors of the IV conversion circuits 101, 102, 103, 104, and the adding circuit 105 are equal and represented by R, the output voltage Vo of the sensor 6 is given by Expression 1. Because Vb1 and R are known in Expression 1, the output current of the photon counting sensor 200 can be obtained by measuring Vo. In other words, the amount of incident light to the photon counting sensor can be measured.

$$Vo = (I1 + I2 + I3 + I4) \times R - 4 \times Vb1 \quad \text{(Expression 1)}$$

As described above, N pixels of the photon counting sensor 200 are for commonized for each of M areas of the photon counting sensor 200 (N>M, M and N are natural numbers). These N pixels are independently converted into voltages by the IV conversion circuits, added and output. As a result, the effects of parasitic components inside the photon counting sensor 200 are dispersed, and it becomes possible for the photon counting sensor 200 to speedily response to the pulse oscillation of the laser light source 2.

Furthermore, in the case of an MPPC (registered trademark) used as the photon counting sensor for example, it is known that, if a high voltage of about 70 V is applied, usually a multiplication factor varies at a voltage of a several V. Therefore, by applying the reference voltage Vb1 to each IV conversion circuit using the voltage setting section 106 shown in FIG. 2, variations between output currents flowing from the respective light incident parts of the photon counting sensor can be adjusted, and the multiplication factor of the photon counting sensor can be controlled.

In other words, owing to the above configuration of the photon counting sensor according to this embodiment, the photon counting sensor can speedily response to the speedy pulse oscillation of the laser light source, and additionally variations of the multiplication factors of the respective photo-detecting elements that are allocated into several hundreds or more of pixels can be kept down, therefore it becomes possible to detect a very small foreign material with a high degree of accuracy. In addition, although the reference voltage Vb1 is applied to all the IV conversion circuits 101 to 104 in common in this embodiment, the reference voltages applied to the IV conversion circuits 101 to 104 can be changed in accordance with the variations of the respective light incident areas, with the result that the multiplication factor of the photon counting sensor can be controlled.

Although an inspection device on which a photon counting sensor is mounted has been described in this embodiment, it is conceivable that a device on which a photon counting sensor is mounted is not only an inspection device but also a semiconductor measurement device or a mass spectroscope.

Figure 6:
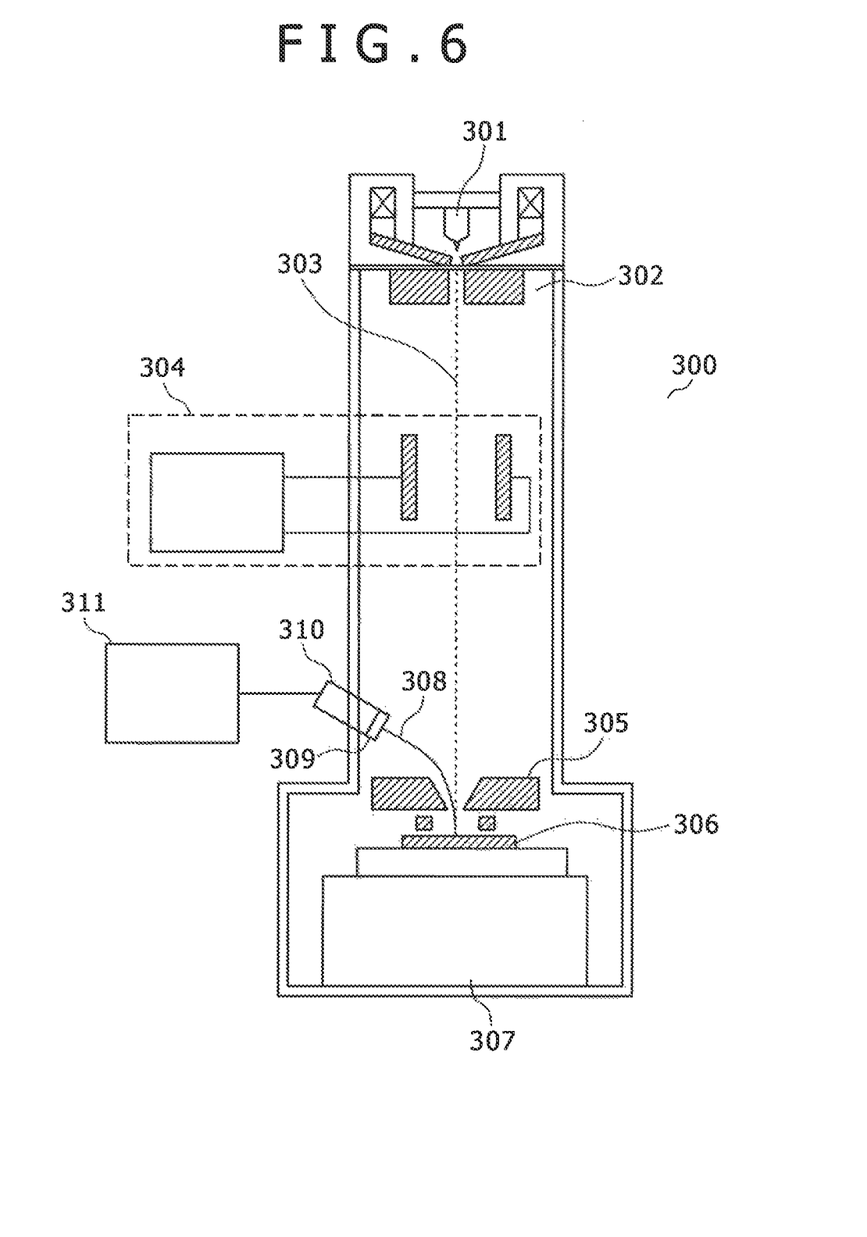
FIG. 6 is an example of a block diagram of a semiconductor measurement device according to the first embodiment.

FIG. 6 shows an example of a block diagram of a semiconductor measurement device. In the semiconductor measurement device 300, an electron beam 303 is generated by an electro gun 301, and a semiconductor wafer 306 disposed on a stage 307 is scanned by the electron beam 303 that has passed through a focusing lens 302, a deflection control unit 304, and an objective lens 305. Secondary electrons 308 are generated from the semiconductor wafer 306 by the irradiation of the electron beam 303, the secondary electrons 308 are detected via a scintillator 309 and a photon counting sensor 310, and the generation and measurement of a detected image or inspection are executed by a data processing unit 311 using the detected secondary electrons 308.

Figure 7:
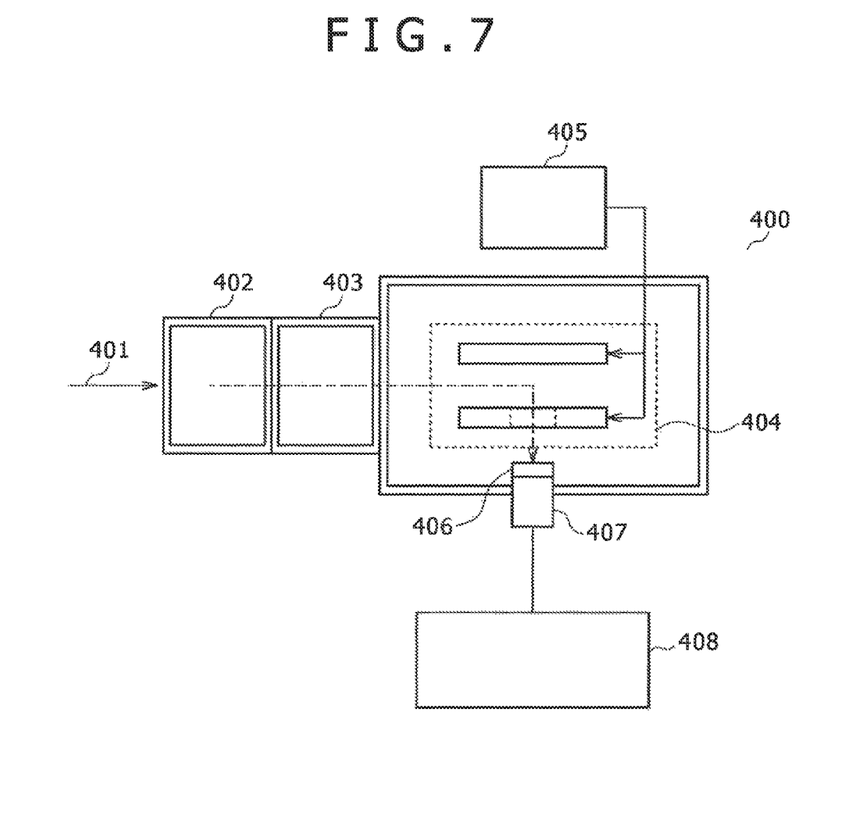
FIG. 7 is an example of a block diagram of a mass spectroscope according to the first embodiment.

FIG. 7 shows an example of a block diagram of a mass spectroscope. In the mass spectroscope, mass spectrometry is executed in such a way that a specimen is ionized, the ions are trapped between the electrodes of a vacuum chamber, high voltages in these electrodes are scanned, the ions, whose masses are corresponding to the respective voltages, are emitted, and these ions are converted into lights by a scintillation, and the lights are detected by a photon counting sensor as signals. In a mass spectroscope 400, specimen gas 401 is injected into a specimen introduction room 402, and the specimen gas is ionized in an ionization room 403. The ionized specimen gas is trapped in an ion trap unit 404, high voltages are scanned from a high voltage application unit 405, and the ions, whose masses correspond to the respective voltages, are detected via a scintillator 406 and a photon counting sensor 407, so that mass spectrometry is executed by a data processing unit 408.

Furthermore, in the following embodiments, a device on which a photon counting sensor is mounted is not limited to an inspection device as is the case with this embodiment.

Second Embodiment

Figure 4:
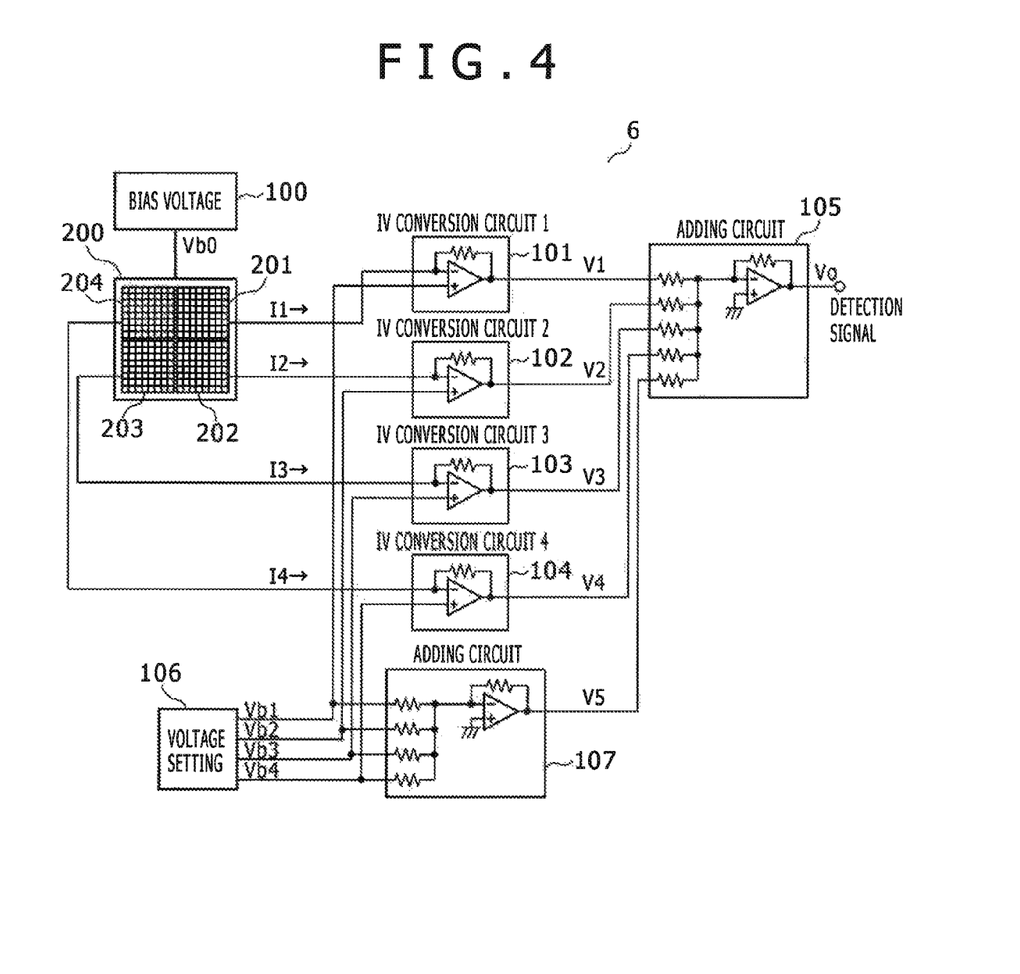
FIG. 4 is an example of a sensor according to a second embodiment.

FIG. 4 is a block diagram showing a second embodiment about a sensor of an inspection device according to the present invention. Hereinafter, for preventing explanations from becoming complicated, explanations about components having the same reference signs as those of components of the first embodiment will be omitted.

A sensor 6 shown in FIG. 4 includes a photon counting sensor 200; a bias voltage setting section 100; IV conversion circuits 101, 102, 103, and 104; adding circuits 105 and 107; and a voltage setting section 106.

In the sensor 6, the voltage setting section 106 outputs reference voltages Vb1, Vb2, Vb3, and Vb4, and bias voltages for the areas 201, 202, 203, and 204 of the photon counting sensor 200 are set variable via the IV conversion circuits 101, 102, 103, and 104 respectively, so that multiplication factors for these areas are respectively set.

In addition, the output voltages of the voltage setting section 106 are added by the adding circuit 107, and eventually a detection signal Vo is obtained as the output voltage of the adding circuit 105. Assuming that all the values of resistors of the sensor 6 are equal and represented by R, the voltages V1, V2, V3, V4, V5, and Vo are given by Expression 2 to 7.

$$V1 = Vb1 - I1 \times R \quad \text{(Expression 2)}$$

$$V2 = Vb2 - I2 \times R \quad \text{(Expression 3)}$$

$$V3 = Vb3 - I3 \times R \quad \text{(Expression 4)}$$

$$V4 = Vb4 - I4 \times R \quad \text{(Expression 5)}$$

$$V5 = -(Vb1 + Vb2 + Vb3 + Vb4) \quad \text{(Expression 6)}$$

$$Vo = (I1 + I2 + I3 + I4) \times R \quad \text{(Expression 7)}$$

According to the configuration of this embodiment, even in the case where there are variations between the multiplication factors of each of the areas of the photo counting sensor, the variations can be adjusted so as to become uniform by setting a reference voltage for each IV conversion circuit. Furthermore, the adding circuit 107, which adds the output voltages of the voltage setting section 106, is installed, and eventually the detection signal Vo is detected by adding the outputs of the IV conversion circuits and the output of the adding circuit 107 using the adding circuit 105, which makes it possible to cancel the voltage outputs from the voltage setting section 106. Therefore, it becomes possible to detect a very small foreign material with a high degree of accuracy.

Although the reference voltages are set for the IV conversion circuits respectively in this embodiment, even if the same reference voltage is applied to all the IV conversion circuits as is the case with the first embodiment, the output voltage from the voltage setting section 106 can be offset, therefore it is possible to detect a very small foreign material with a high degree of accuracy.

Third Embodiment

Figure 5:
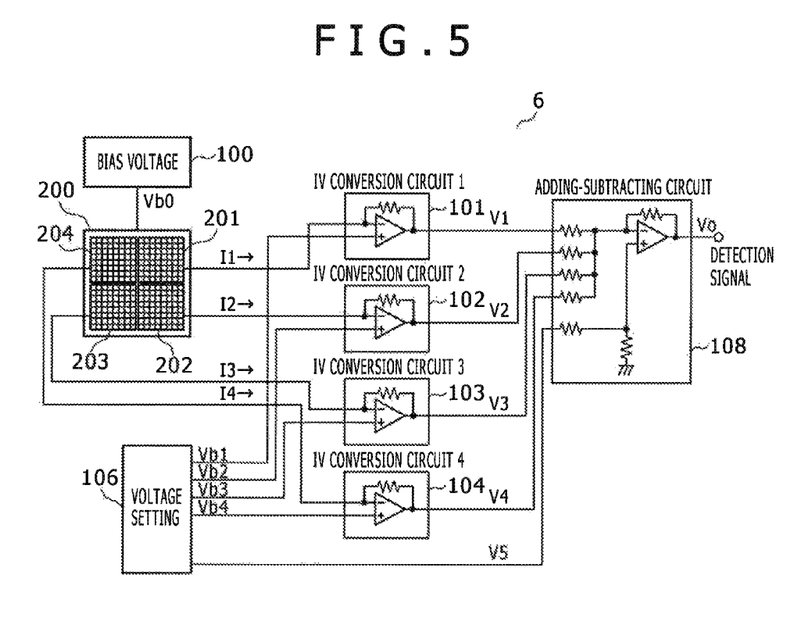
FIG. 5 is an example of a sensor according to a third embodiment.

FIG. 5 is a block diagram showing a third embodiment about a sensor of an inspection device according to the present invention. Hereinafter, for preventing explanations from becoming complicated, explanations about components having the same reference signs as those of components of the first embodiment will be omitted.

A sensor 6 shown in FIG. 4 includes a photon counting sensor 200; a bias voltage setting section 100; IV conversion circuits 101, 102, 103, and 104; an adding-subtracting circuit 108; and a voltage setting section 106.

As is the case with the second embodiment, in the sensor 6, the voltage setting section 106 outputs reference voltages Vb1, Vb2, Vb3, and Vb4, and bias voltages for the areas 201, 202, 203, and 204 of the photon counting sensor 200 are set variable via the IV conversion circuits 101, 102, 103, and 104 respectively, so that multiplication factors are respectively set for these areas. Here, the outputs of the IV conversion circuits 101, 102, 103, and 104 are given by the above Expressions 2 to 5 respectively. In addition, a voltage V5 equal to the summation of Vb1 to Vb4 is output from the voltage setting section 106, and herewith, a detection signal Vo, which is given by the above Expression 7, is obtained as the output voltage of the adding-subtracting circuit 108.

According to the configuration of this embodiment, even in the case where there are variations between the multiplication factors of the areas of the photo counting sensor, the variations can be set uniform by setting a reference voltage for each IV conversion circuit. Furthermore, because the voltage V5 equal to the summation of Vb1 to Vb4 is output from the voltage setting section 106, and eventually the detection signal Vo is output by the adding-subtracting circuit 108, the output voltages from the voltage setting section 106 can be canceled, which makes it possible to detect a very small foreign material with a high degree of accuracy.

Up to now, in the first to third embodiments, although it has been explained that the photon counting sensor including N pixels is commonized for each of four areas, independently converted into voltages by the relevant IV conversion circuits, added and output, and that bias voltages for the respective areas are independently controlled using the voltage setting section and the IV conversion sections, it goes without saying that the number M of the areas of the photon counting sensor can be arbitrary as long as N>M, and the number of pixels included in each area is not necessarily equal to N/M.

In addition, as for the voltage setting section, it goes without saying that an advantageous effect similar to the advantageous effects obtained in the above-described first to third embodiments can be obtained in the case where a CPU or a user program (not shown) can variably control the reference voltage or reference voltages in accordance with the operation compensation of the photon counting sensor for temperature variation or the usage status of the inspection device, and at the same time an arbitrary reference voltage or arbitrary reference voltages are set for IV conversion circuits without using the voltage setting section.

Furthermore, the present invention is not limited to the above-described embodiments, and various modification examples can be included in the present invention. For example, the above first to third embodiments have been described in detail in order to make the present invention easy to understand, and therefore all the components described so far are not always indispensable for the present invention. In addition, a part of the configuration of one embodiment can be replaced with a part of configuration of another embodiment, or a new embodiment may be made by adding a part of the configuration of one embodiment to the configuration of another embodiment. In addition, a new embodiment of the present invention may be made by adding a different configuration to a part of the configuration of each embodiment, deleting a part of the configuration from each embodiment, or replacing a part of configuration of each embodiment with a different configuration.

In the first to third embodiments, the sensor 6 has been described as a device applied to an inspection device for inspecting a wafer, but the sensor 6 can be applied to other devices such as a measurement device and a medical/healthcare device as long as the devices uses a photon counting sensor as a detection section, which makes it possible for the devices to execute detection with a high degree of accuracy.

Furthermore, it is conceivable that parts of or the entireties of the above-described configurations, functions, processing units, processing sections, and the like are realized by hardware using integrated circuits, for example. Alternatively, the above configurations, functions, and the like can be realized by software in such a way that the CPU 10 interprets programs for realizing the above functions and the like, and executing the programs. Information included in programs, tables, files, and the like, which realize the above functions and the like, can be stored in recording devices such as memories, hard disks, and SSDs (solid state drives), or in recording media such as IC cards, SD cards, and DVDs.

In addition, in the above-described drawings, control lines and information lines are shown in the case where they are indispensable for explaining the above embodiments, therefore all control lines and information lines are not necessarily shown for a product. It is conceivable that in reality almost all components in almost every embodiment are interconnected.

LIST OF REFERENCE SIGNS 1, 306: wafer
2: laser light source
3: light reflector
4, 5: lens
6: sensor
7: amplification circuit
8: A/D conversion circuit
9: data processing unit
10: CPU
11: map output unit
12: stage control unit
13: rotary stage
14: translational stage
20: clock detection unit
21: sensor
22: IV conversion circuit
23: clock regeneration circuit
24: delay adjustment unit
50: inspection device
100: bias voltage setting section
101, 102, 103, 104: IV conversion circuit
105, 107: adding circuit
106: voltage setting section
108: adding-subtracting circuit
200, 310, 407: photon counting sensor
300: semiconductor measurement device
301: electro gun
302: focusing lens
303: electron beam
304: deflection control unit
305: objective lens
307: stage
308: secondary electron
309, 406: scintillator
311: data processing unit
400: mass spectroscope
401: specimen gas
402: specimen introduction room
403: ionization room
404: ion trap unit
405: high voltage application unit
408: mass spectroscopic unit

The invention claimed is:
1. An electron beam device comprising:
an irradiation system for supplying an electron beam to a specimen; and
a detection system for detecting electrons from the specimen,
wherein the detection system includes:
a photon counting sensor that outputs M output signals from photo-detecting elements of N pixels, wherein M and N are natural numbers, and M<N;
M current-voltage conversion units that execute current-voltage conversion on the output signals of the photon counting sensor respectively;
a voltage application unit that applies reference voltages to the current-voltage conversion units; and a detection signal generation unit that generates a detection signal on the basis of the outputs of the current-voltage conversion sections;

wherein the reference voltages are input to the positive inputs of the power source voltage conversion units, and the output signals of the photon counting sensor are input to the negative inputs of the power source voltage conversion units, and wherein an adding circuit that inverse-point-adds the output voltages from the voltage application unit is included, and the summation of the output from the adding circuit and the outputs from the current-voltage conversion units are input to the detection signal generation unit.

2. A medical device comprising:

a photon counting sensor that outputs M output signals from photo-detecting elements of N pixels, wherein M and N are natural numbers, and M<N;

M current-voltage conversion units that execute current-voltage conversion on the output signals of the photon counting sensor respectively;

a voltage application unit that applies reference voltages to the current-voltage conversion units; and a detection signal generation unit that generates a detection signal on the basis of the outputs of the current-voltage conversion units;

wherein the reference voltages are input to the positive inputs of the power source voltage conversion units, and the output signals of the photon counting sensor are input to the negative inputs of the power source voltage conversion units, and wherein an adding circuit that inverse-point-adds the output voltages from the voltage application unit is included, and the summation of the output from the adding circuit and the outputs from the current-voltage conversion units are input to the detection signal generation unit.

3. The device according to claim 1, wherein the voltage application section applies the same reference voltages to the M current-voltage conversion sections.

4. The device according to claim 2, wherein the detection section includes an addition section that adds the outputs of the voltage application section; and the detection signal generation section generates a detection signal on the basis of the outputs of the current-voltage conversion sections and the output of the addition section.

5. The device according to claim 1, wherein the voltage application section outputs the total value of voltages applied to the current-voltage conversion sections, and the detection signal generation section generates a detection signal by adding the outputs of the current-voltage sections and subtracting the total value.

6. The device according to claim 1, wherein, the photon counting sensor commonizes the photo-detecting elements of the N pixels for each area in which the photo-detecting elements are allocated and outputs M output signals, and the voltage application section sets voltages to be applied to the current-voltage conversion sections on the basis of variations between the output signals of the areas to which the photo-detecting elements are allocated.

* * * * *